Figure 1:
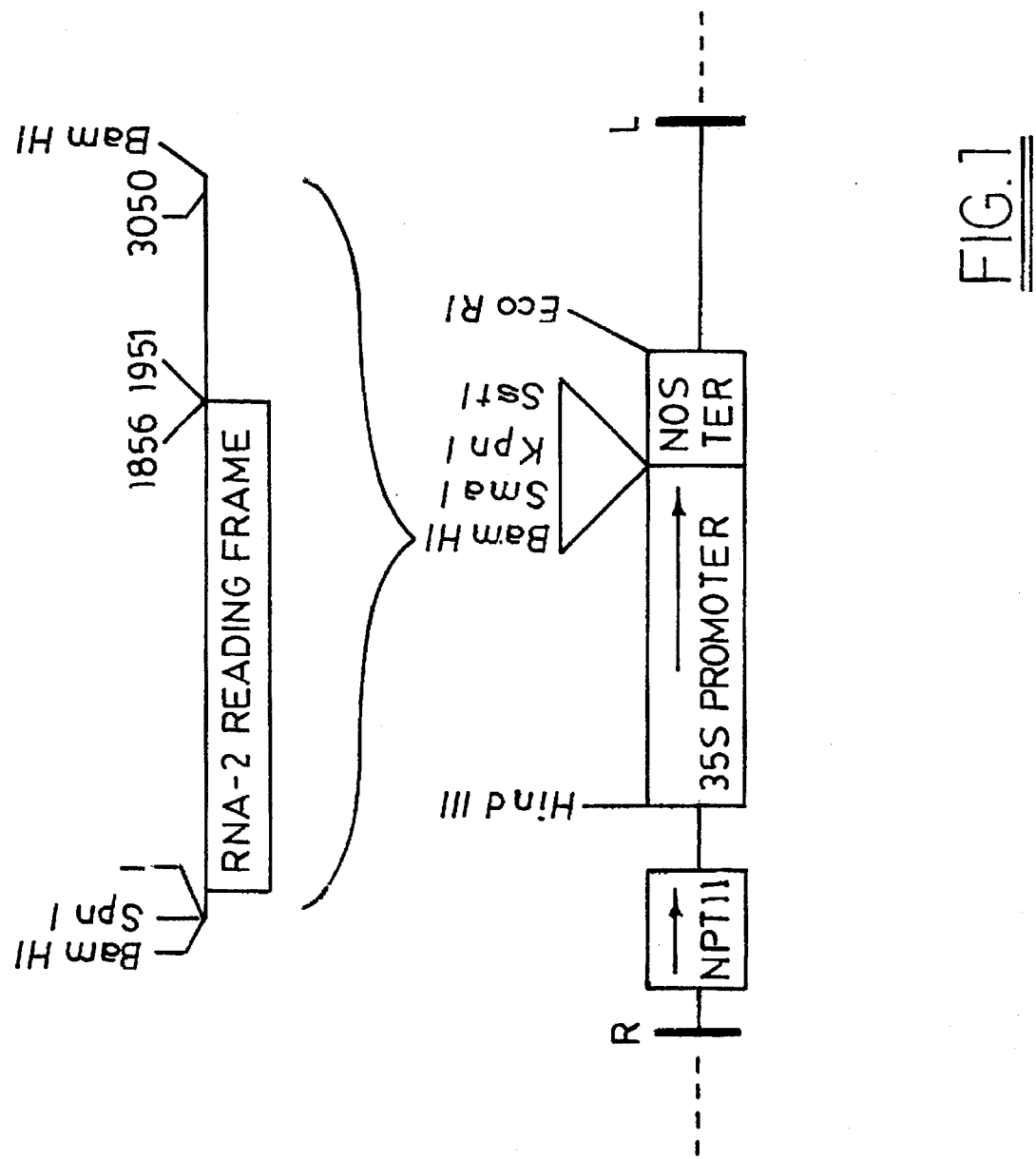

US005633449A

United States Patent [19]
Zaitlin et al.

[11] Patent Number: 5,633,449
[45] Date of Patent: May 27, 1997

[54] INDUCTION OF RESISTANCE TO VIRAL DISEASES IN PLANTS

[75] Inventors: Milton Zaitlin; Peter Palukaitis, both of Ithaca, N.Y.

[73] Assignee: Cornell Research Foundation, Inc., Ithaca, N.Y.

[21] Appl. No.: 479,577

[22] Filed: Jun. 7, 1995

Related U.S. Application Data

[63] Continuation of Ser. No. 197,096, Feb. 15, 1994, abandoned, which is a continuation-in-part of Ser. No. 894,064, Jun. 8, 1992, abandoned, which is a continuation-in-part of Ser. No. 491,473, Mar. 12, 1990, abandoned.

[51] Int. Cl.$^6$ ............................ A01H 4/00; C12N 15/82; C12N 5/14
[52] U.S. Cl. .................. 800/205; 800/250; 800/DIG. 43; 536/23.2; 435/320.1; 435/172.3; 435/418; 435/419
[58] Field of Search .......................... 435/172.3, 320.1, 435/240.4, 235.1; 800/205, DIG. 43, 250; 536/23.2

[56] References Cited

U.S. PATENT DOCUMENTS

| | | | |
|---|---|---|---|
| 4,774,182 | 9/1988 | Szybalski | 435/69.1 |
| 5,240,841 | 8/1993 | Johnston et al. | 435/172.3 |
| 5,503,999 | 4/1996 | Jilka et al. | 435/172.3 |
| 5,510,253 | 4/1996 | Mitsky et al. | 435/172.3 |

FOREIGN PATENT DOCUMENTS

| | | |
|---|---|---|
| 278627 | 1/1988 | European Pat. Off. . |
| 421376 | 10/1990 | European Pat. Off. . |
| 426195 | 11/1990 | European Pat. Off. . |
| 536106 | 10/1992 | European Pat. Off. . |
| WO89/08145 | 9/1989 | WIPO . |
| WO90/13654 | 11/1990 | WIPO . |
| WO91/13542 | 9/1991 | WIPO . |
| WO91/16420 | 10/1991 | WIPO . |
| WO92/03539 | 3/1992 | WIPO . |
| WO93/21329 | 10/1993 | WIPO . |
| WO94/18336 | 8/1994 | WIPO . |

OTHER PUBLICATIONS

Rezaian et al (1988) Plant Molecular Biology vol. 11: pp. 463–471.
Rizzo et al (1988) Journal Gen. Virology vol. 69: pp. 1777–1787.
Goelet et al., "Nucleotide Sequence of Tobacco Mosaic Virus RNA," *Proc. Natl. Acad. Sci. USA* 79:5818–22 (1982).
Sulzinski et al., "Replication of Tobacco Mosaic Virus," *Virology* 145:134–40 (1985).
Powell et al., "Protection Against Tobacco Mosaic Virus in Transgenic Plants that Express Tobacco Mosaic Virus Antisense RNA," *Proc. Natl. Acad. Sci. USA* 86:6949–52 (1989).
van Dun et al., "Transgenic Tobacco Expressing Tobacco Streak Virus or Mutated Alfalfa Mosaic Virus Coat Protein Does Not Cross–protect Against Alfalfa Mosaic Virus Infection," *Virology* 164:383–89 (1988).

Abel et al., "Delay of Disease Development in Transgenic Plants that Express the Tobacco Mosaic Virus Coat Protein Gene," *Science* 232:738–43 (1986).
Carr et al., "Resistance to Tobacco Mosaic Virus Induced by the 54–kDa Gene Sequence Requires Expression of the 54–kDa Protein," *Molecular Plant–Microbe Interactions* 5(5):397–04 (1992).
J.A. Bruenn, "Relationships Among the Positive Strand and Double–strand RNA Virus as Viewed Through Their RNA–dependent RNA Polymerases," *Nucleic Acids Research* 19(2):217–26 (1991).
Young et al., "Tobacco Mosaic Virus Replicase and Replicative Structures," *J. Cell Sci. Suppl.* 7:277–85 (1987).
MacFarlane et al., "Plants Transformed with a Region of the 201–kilodalton Replicase Gene From Pea Early Browning Virus RNA1 are Resistant to Virus Infection," *Proc. Natl. Acad. Sci. USA* 89:5829–33 (1992).
Lindbo et al., "Pathogen–derived Resistance to a Potyvirus: Immune and Resistant Phenotypes in Transgenic Tobacco Expressing Altered Forms of a Potyvirus Coat Protein Nucleotide Sequence," *Molecular Plant–Microbe Interactions* 5(2):144–53 (1992).
Golemboski et al., "Plants Transformed with a Tobacco Mosaic Virus Nonstructural Gene Sequence are Resistant to the Virus," *Proc. Natl. Acad. Sci. USA* 87:6311–15 (1990).
Carr et al., "Resistance in Transgenic Tobacco Plants Expressing a Nonstructural Gene Sequence of Tobacco Mosaic Virus is a Consequence of Markedly Reduced Virus Replication," *Molecular Plant–Microbe Interactions* 4(6):579–85 (1991).
Anderson et al., "A Defective Replicase Gene Induces Resistance to Cucumber Mosaic Virus in Transgenic Tobacco Plants," *Proc. Natl. Acad. Sci. USA* 89:8759–63 (1992).
Young et al., "Using Plant Virus and Related RNA Sequences to Control Gene Expression," *19th Stadler Genetics Symposium* (1989).
Young et al., "Barley Yellow Dwarf Virus Expression in Wheat Protoplasis and Construction of Synthetic Genes to Interfere with Viral Replication," *J. Cell. Biochem. Suppl.* *13D* M552 (1989).
Inokuchi et al., "Interference with Viral Infection by Defective RNA Replicase," *Journal of Virology* 61(12):3946–49 (1987).

(List continued on next page.)

*Primary Examiner*—Che S. Chereskin
*Attorney, Agent, or Firm*—Nixon, Hargrave, Devans & Doyle

[57] ABSTRACT

The present invention describes a method for the induction of resistance in a plant host to a RNA or DNA virus pathogenic to the plant which comprises isolating a fragment of viral RNA or DNA associated with the replicase portion of the virus genome, specifically a portion that does not involve a read-through portion of the gene, and integrating a DNA copy of the isolated fragment or a portion thereof into the genome of a recipient plant in such a manner that the plant becomes transformed with the inserted fragment.

22 Claims, 3 Drawing Sheets

OTHER PUBLICATIONS

Ishikawa et al., "In vitro Mutagenesis of the Putative Replicase Gene of Tobacco Mosaic Virus," *Nucleic Acids Research* 14(21):8291–05 (1986).

White et al., "In vitro Replication of Tobacco Mosaic Virus RNA in Tobacco Callus Cultures: Solubilization of Membrane–bound Replicase and Partial Purification," *Journal of Virology* 21(2):484–92 (1977).

Beachy et al., "Characterization and In vitro Translation of the RNAs from Less–than–full–length, Virus–related, Nucleoprotein Rods Present in Tobacco Mosaic Virus Preparations," *Virology* 81:160–69 (1977).

Meshi et al., "Two Concomitant Base Substitutions in the Putative Replicase Genes of Tobacco Mosaic Virus Confer the Ability to Overcome the Effects of a Tomato Resistance Gene, Tm–1," *The EMBO Journal* 7(6):1575–81 (1988).

Rezaian et al., "Anti–sense RNAs of Cucumber Mosaic Virus in Transgenic Plants Assessed for Control of the Virus," *Plant Molecular Biology* 11:463–71 (1988).

Tenllado et al., "*Nicotiana benthamiana* Plants Transformed with the 54 kDa Region of the Pepper Mild Motle Tobamovirus Replicase Gene Exhibit Two Types of Resistance Responses Against Viral Infection," CSIC, Velazquez 144, 28006 Madrid, Spain (1995).

Tenllado et al., "Tobacco Plants Transformed with the 54kDa Region of the PMMV Replicase Gene are Resistant to Virus Infection," CSIC, Velazquez 144, 28006 Madrid, Spain date ?.

Donson et al., "Broad Resistance to Tobamoviruses is Mediated by a Modified Tobacco Mosaic Virus Replicase Transgene," *Molecular Plant–Microbe Interactions* 6(5):635–42 (1993).

Grumet et al., "Pathogen–derived Resistance to Viral Infection Using a Negative Regulatory Molecule," *Virology* 161:561–69 (1987).

F. Tenllado, et al., "Tobacco Plants Transformed With The 54kDa Region Of The PMMV Replicase Gene Are Resistant To Virus Infection," CSIC, Velazquez 144, 28006 Madrid, Spain (1993).

Skuzeski, J.M., et al., "Analysis of leaky viral translation termination codons in vivo by transient expression of improved β–glucuronidase vectors," *Plant Molecular Biology*, 15:65–79 (1990).

Zaccomer, B., et al., "The remarkable variety of plant RNA virus genomes," *Journal of General Virology*, 76:231–247 (1995).

Audy, P., et al., "Replicase–Mediated Resistance To Potato Virus Y in Transgenic Tobacco Plants," *MPMI*, 7(1):15–22 (1994).

Braun, C.J., et al., "Expression of Amino–Terminal Portions or Full–Length Viral Replicase Genes in Transgenic Plants Confers Resistance to Potato Virus X Infection," *The Plant Cell*, 4:735–744 (1992).

Rizzo, T.M., "Nucleotide Sequence and Evolutionary Relationships of Cucumber Mosaic Virus (CMV) Strains: CMV RNA 2," *J. gen. Virol.*, 69:1777–1787 (1988).

Longstaff, M., et al., "Extreme resistance to potato virus X infection in plants expressing a modified component of the putative viral replicase," *The EMBO Journal*, 12(2):379–386 (1993).

Sijen, T., et al., "Replication of Cowpea Mosaic Virus RNA1 or RNA2 Is Specifically Blocked in Transgenic *Nicotiana benthamiana* Plants Expressing the Full–Length Replicase or Movement Protein Genes.," *MPMI*, 8(3): (1995).

Kaniewski, W., et al., "Expression of Potato Leafroll Virus (PLRV) Replicase Genes in Russet Burbank Potatoes Provide Field to PLRV," *Abstracts*, P1–32. Jul. 9–13, 1994.

Brederode, F., et al., "Replicase–Mediated Resistance to Alfalfa Mosaic Virus," *Virology*, 207:467–474 (1995).

Sijen, T., et al., "Expression of CPMV Replicase or Movement Genes in Transgenic *Nicotiana benthamiana* Plants Confers Resistance to CPMV Infection," Dept. of Molecular Biology, Wageningen Agricultural University, Dreijenlaan 3,6703 HA, Wageningen, The Netherlands. (Jul. 1994) EMBO Workshop.

Zaitlin, M., et al., "Specificity of Replicase–Mediated Resistance to Cucumber Mosaic Virus," *Virology*, 201:200–205 (1994).

Gonsalves, C., et al., "Transferring Cucumber Mosaic Virus–White Leaf Strain Coat Protein Gene into *Cucumis melo* L. and Transgenic Plants for Protection against Infections," *J. Amer. Soc. Hort. Sci.*, 119(2):345–355 (1994).

Gonsalves, et al., "Comparison of Coat Protein–Mediated and Genetically–Derived Resistance in Cucumbers to Infection by Cucumber Mosaic Virus Under Field Conditions with Natural Challenge Inoculations by Vectors," Department of Plant Pathology, Cornell University, New York State Agricultural Experiment Station, Geneva, NY 14456. Bio/Technology 16:1564–1570, 1992.

Grumet, R., et al., "Pathogen–Derived Resistance to Viral Infection Using a Negative Regulatory Molecule," *Virology*, 161;561–569 (1987).

van Dun, C.M., et al., "Expression of Alfalfa Mosaic Virus cDNA1 and 2 in Transgenic Tobacco Plants," *Virology*, 163:572–578 (1988).

Mori, M., et al., "Expression of brome mosaic virus–encoded replicase genes in transgenic tobacco plants," *Journal of General* 73:169–172 (1992).

Rubino, et al., "Resistance to Cymbidiium Ringspot Tombusvirus Infection in Transgenic *Nicotiana benthamiana* Plants Expressing a Full–Length Viral Replicase Gene," Dipartimento di Protezione della Piante, Universita degli Studi, and Centro di Studio del CNR sui Virus el le Virosi delle Colture Mediterranee, Bari, Italy (1993). Molecular Plant–Microbe Interactions 6:729.

Rezaian, M. A., et al., "Anti–sense RNAs of cucumber mosaic virus in transgenic plants assessed for control of the virus," *Plant Molecular Biology*, 11:463–471 (1988).

Carr, J.P., et al., "Replicase–mediated resistance," *seminars in Virology*, 4:339–347 (1993).

Cuozzo, et al (May 1988) Bio/Technology 6: 549–557.

INDUCTION OF RESISTANCE TO VIRAL DISEASES IN PLANTS

This application is a continuation of U.S. patent application Ser. No. 08/197,096, filed Feb. 15, 1994, now abandoned, which is a continuation-in-part of application Ser. No. 07/894,064, filed Jun. 8, 1992, now abandoned, which is a continuation-in-part of application Ser. No. 07/491,473, filed Mar.12, 1990, now abandoned.

BACKGROUND OF THE INVENTION

Since the 1986 paper of P. Powell-Abel et al [see Science 223:738] showing that plants transformed with and expressing the coat protein gene of tobacco mosaic virus (TMV) are resistant to TMV, there have been a nunnber of other examples of this concept which will undoubtedly have important implications for the protection of many crop species from various viral infections. To date, for example, viral coat protein-mediated resistance has been shown with at least 25 viruses in 15 taxonomic groups including alfalfa mosaic virus, tobacco rattle virus, potato virus X, cucumber mosaic virus (CMV), potyviruses, and plants transformed with both potato virus X and potato virus Y coat protein.

Plant virus sequences other than those coding for the viral coat protein have been tested to determine if transformed plants can be made to exhibit resistance to post-transformation viral infection. Positive sense sequences of alfalfa mosaic virus comprising almost full length copies of RNAs 1 and 2 failed to induce resistance in transformed plants [see Virology 163:572 (1988)]; anti-sense sequences of the TMV and potato virus coat protein genes did induce a low level of resistance in transformed tobacco [see Proc. Natl. Acad. Sci., USA 86:6949 (1989); and EMBO Journal 7:1273 (1988)]; likewise antisense RNAs from one of three regions tested (5' sequences or RNA 1) of the CMV genome gave a low level of resistance in only a single transformant line.

Other forms of resistance using plant transformations with DNAs prepared from satellite RNAs of plant viruses have been reported, such as the use of the satellite of CMV [see Nature 328:799 (1987)] and the concept of the ribozyme based on sequences from satellite RNAs which possess the capacity to self cleave [see Nature 334:585 (1988)].

SUMMARY OF THE INVENTION

The invention described herein represents an entirely new type of virus-induced resistance which may be transferred from one plant generation to another. The present invention discloses that transgenic plants containing a coding sequence taken from all or part of the replicase portion, specifically a portion that does not involve a read-through replicase gene, of the viral genome, are resistant to subsequent disease by the virus; although there may be a very benign degree of virus synthesis in the inoculated leaf, the virus has been found not to spread and hence no disease develops. In the description which follows, the use of a modified cDNA of RNA-2 which encodes one component of the replicase of cucumber mosaic virus is described as one specific example of the broader technology according to the present invention. Thus, in its broadest aspects, the present invention defines a means for bringing about viral resistance in plants which have been transformed with DNA copies of fragments or segments taken from the replicase portion of the pathogenic virus genome. In addition, the present invention defines transformed plants and their seeds which carry a portion of the viral genome which codes for a portion of the replicase genome of the pathogenic virus. According to the present invention, transformed plants that contain a portion of the viral replicase gene within their genome are resistant to subsequent viral disease from the virus from which the portion was derived, and these plants may also be resistant to subsequent disease from other closely related viruses.

Accordingly, a novel aspect of the present invention, is the conveyance of viral resistance to a plant which has previously undergone transformation of its normal genome with a portion of the replicase region of a viral genome, in its "sense" orientation.

A more complete understanding of this aspect, as well as others of the present invention, can be had by reference to the following figures and examples.

BRIEF DESCRIPTION OF THE DRAWINGS

FIG. 1 depicts the plant expression vector containing the modified Fny-CMV RNA-2 gene sequence inserted between the CaMV 35S promoter and the nopaline synthase polyadenlyation site;

FIG. 2 depicts the construction of a modified Fny-CMV RNA-2 gene for integration into the genome of a host plant;

DETAILED DESCRIPTION OF THE INVENTION AND DRAWINGS

More specifically, FIG. 1 shows the plant expression vector containing the modified Fny-CMV RNA-2 gene sequence according to the present invention inserted between the CaMV 35S promoter (35S) and the nopaline synthase polyadenlyation site (NOS polyA). This plasmid (pCMV N/B-23), as will be described in detail within the following specification, was derived by inserting the modified Fny-CMV RNA-2 gene according to the present invention into the BamHI site of pROK2, a binary plant transformation vector [see Nature 321:446 (1986)]. This was accomplished by digesting pFny N/B-4 with SphI which cut this plasmid at a site 5' of the RNA-2 cDNA sequences. A BamHI-SphI adapter was ligated to this SphI site and then digested with BamHI which cuts at a site 3' of the RNA-2 sequences, thereby liberating the entire modified cDNA molecule. This 3 kb fragment was subcloned via standard techniques into the BamHI site of pROK2 to generate pCMV N/B-23. Prior to plant transformation, this construct was transferred to *Agrobacterium tumefaciens* strain LBA-4404 by tri-parental mating [see Methods Enzymol. 118:627 (1986)] mediated by *E. coli* strain MM294-pRK2013. The trans-conjugates were selected by resistance to kanamycin and streptomycin at 50 and 125 μg/ml, respectively. The numbers in the figure refers to nucleotides in the Fny-CMV RNA-2 sequence; the neomycin phosophotransferase II (NPTII) gene confers a selectable kanamycin resistance marker on transformed plants; LB and RB=the left and right border of DNA transferred to the plant genome during *Agrobacterium tumefaciens*-mediated plant transformation; Ori=origin of replication.

FIG. 2 shows the construction of pCMV N/B-23 being done in two stages. First a 94 basepair region was deleted from the full length cDNA clone of Fny-CMV RNA-2. Second, this deletion derivative was subcloned into pROK2, the plant transformation vector.

As described more completely in Example II, the plasmid pFny206 containing the full length cDNA clone of Fny-CMV RNA-2 in pIBI-76, was digested with the restriction enzymes NcoI and BstEII. This DNA was then treated with the Klenow fragment of *E. coli* DNA polymerase 1 which acts as a DNA modification enzyme to obtain a blunt ended molecule. This blunt ended DNA was then ligated and transformed by standard methods into *E. coli* JM 101. The plasmid which resulted from this was named pFnyN/B-4. This plasmid was analyzed by various restriction enzyme digestions and DNA sequencing and was shown to have a 94 basepair deletion. This deletion also resulted in a change in the open reading frame such that this gene now encoded a truncated protein of approximately 75 kDa. Cloning also resulted in the retention of an AUG as a potential translation initiator 87 nucleotides upstream of the AUG in the RNA 2 gene resulting in potential translation of an additional 29 amino acids at the amino terminus of the protein.

As further described in Examples II and III, this modified Fny-CMV RNA-2 gene contained in pN/B-4 was subcloned into plant transformation vector pROK2. To facilitate this subcloning, a BamH1 site was added to the 5' end of this gene. pN/B-4 was digested with Sph1 and a BamH1-Sph1 adaptor was ligated to this Sph1 site located at the 5' end of the gene. Following this ligation reaction, the pB/N-4 was digested with BamH1 which released a fragment approximately 2960 basepairs in size containing BamH1 cohesive ends at both the 5' and 3' terminals. It was this fragment which was ligated to the BamH1 site in pROK2, and the resulting plasmid was named pCMV N/B-23. This plasmid was used to transfer this modified Fny-CMV RNA-2 gene into tobacco for further testing described beginning with Example XIII.

Figure 2A:
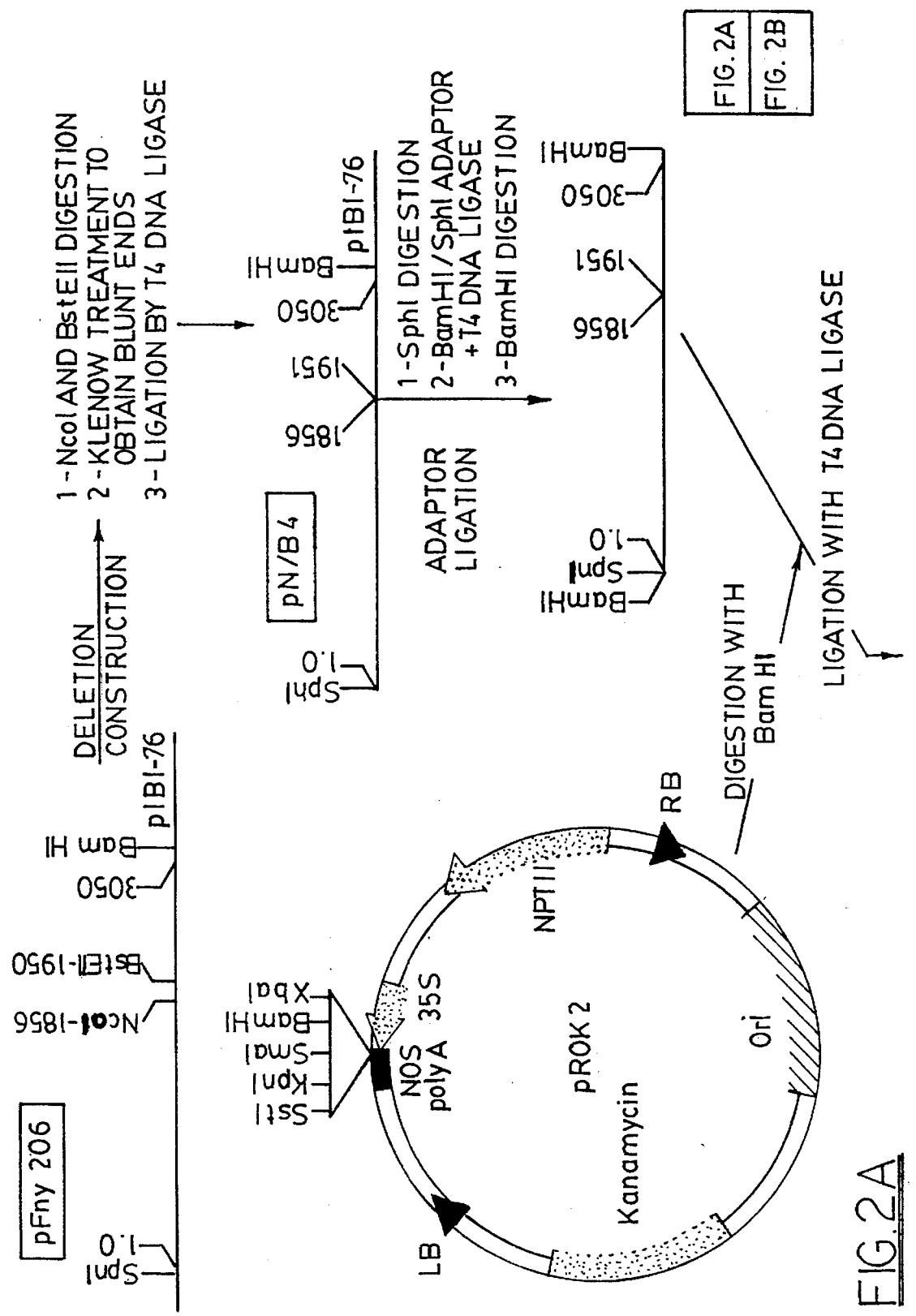
Figure 2B:
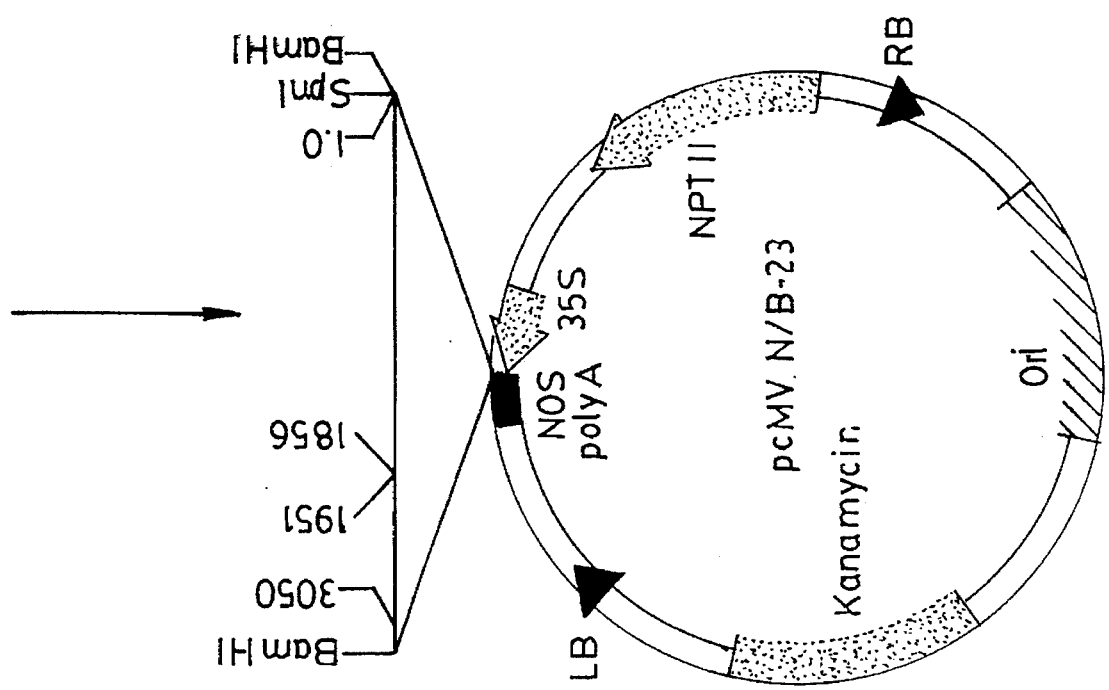

With specific regard to FIG. 2, the plants are named in a code indicating which construct of Fny-CMV RNA-2 was transformed into the plant, what culture was used in a particular transformation, and the particular regenerated plant. "N/B" indicates which construct of Fny-CMV RNA-2 was transformed into a particular plant; in the case of N/B 1-8, the construct in this plant is from pCMV N/B-23 (FIG. 1). The numbers "1" or "2" indicate which of two culture tubes were used to transform tobacco with the N/B construct. The second number appearing in the designation simply indicates the particular plant number. For example, the numeral "8" in the above example simply indicates that this is the eighth regenerated plant obtained in this transformation experiment.

Studies were conducted using cucumber mosaic virus (CMV) as just one example of a preferred embodiment according to the present invention. Cucumber mosaic virus has a tripartite single-stranded RNA plus-sense genome. RNAs 1 and 2 (3.4 kb and 3.0 kb, respectively) code for the 1a and 2a proteins (111 kDa and 97 kDa, respectively) both of which are components of the viral replicase. RNA 3 is dicistronic, coding for the 3a movement protein and the coat protein, the latter of which is translated from the subgenomic RNA 4, derived from RNA 3. CMV strains have been divided into two major subgroups, I and II, that are characterized in accordance with serological, hybridization, nucleotide sequence and coat protein data.

In the experiments described herein, *Nicotiana tabacum* cv. Turkish Samsun NN plants were untransformed or transformed [see Proc. Natl. Acad. Sci USA 89:8759 (1992)] with a modified cDNA clone of RNA-2, which encodes a transcript of the replicase component of CMV subgroup I strain Fny. The gene had been modified by deleting a 94 bp region spanning nucleotides 1857 to 1950 (FIG. 1). More specifically, the partial nucleotide sequence of the Fny-CMV RNA-2 cDNA clone which was modified as described in Example XII and which contains the NcoI and BstEII sites used to generate a 94 basepair deletion is (as RNA) (SEQ. ID. NO. 1):

| AAU ACC AUC GUC A<u>CC</u> <u>AUG</u> GCU GAG UUU GCC UGG UGU UAU GAC | 42 |
| ACC GAC CAA UUC GAA AAG CUU UUA UUC UCA GGC GAU GAU UCU | 84 |
| CUA GGA UUU UCA CUG CUU CCC CCU GUU <u>GGU</u> <u>GAC</u> CCG AGU AAA | 126 |
| UUC ACA | 132 | in which the first underlined portion corresponds to the Nco I restriction site and the bold "G" corresponds to nucleotide 1856, and in which the second underlined portion corresponds to the Bst EII restriction site and the bold "G" corresponds to nucleotide 1951 [see Proc. Natl, Acad. Sci. USA 89:8759 (1992)]. The amino acid sequence encoded by the nucleotide sequence shown above is (SEQ. ID. NO. 2):

Asn Thr Ile Val Thr Met Ala Glu Phe Ala Trp Cys Tyr Asp Thr
            5               10              15

Asp Gln Phe Glu Lys Leu Leu Phe Ser Gly Asp Asp Ser Leu Gly
           20               25              30

Phe Ser Leu Leu Pro Pro Val Gly Asp Pro Ser Lys Phe Thr
           35               40

Once the 94 nucleotide deletion has been made as described in Example XII, the nucleotide sequence at the junction of the deletion is the modified Fny-cDNA clone (as RNA) is (SEQ. ID. NO. 3):

| ACC AUC GUC A<u>CC</u> <u>AUG</u> GUG ACC CGA GUA AAU UCA CAA CUC UUU | 42 |
| UCA ACA UGG AAG CUA AGG UGA | 63 | in which the underlined portion corresponds to the prior underlined restriction sites and the bold "G"'s represent original nucleotides 1856 and 1951. The amino acid sequence for this region, leading to a frame shiftted and truncated protein is (SEQ. ID. NO. 4):

Thr Ile Val Thr Met Val Thr Arg Val Asn Ser Gln Leu Phe Ser
           5               10             15

Thr Trp Lys Leu Arg
       20

The region surrounding and including this 94 bp region contains four domains which are highly conserved among putative replicase encoding sequences in many positive-sense RNA plant and animal viruses. This deleted 94 bp region also contained the third domain, the Gly-Asp-Asp domain, which has been shown to be necessary for replication of the bacteriophage Qβ. As noted in the sequence above, this deletion also caused a shift in the open reading frame resulting in a truncated translation product. $R_1$ generation plants from the original transformants were tested for resistance to virus infection. Individual plants from 2 out of 18 transformed lines were resistant to systemic disease when inoculated with either Fny-CMV virions or RNA at concentrations as high as 500 μg/ml.

Various generations of the transformed plants of Line 2, Lines $R_2$-2, $R_3$-2 and $R_4$-2 were derived from $R_1$ Line 1-8, and the generations of Line 5, Lines $R_2$-5, $R_3$-5, and $R_4$-5 were derived from $R_1$ Line 1-2 of Anderson [see Proc. Natl. Acad. Sci 89:8759 (1992)]. In all cases, plants selected to be selfed to produce seed for subsequent generations were first tested and determined to be resistant to Fny-CMV (100 μg/ml virus).

The sources of CMV strains and other viruses, and the hosts from which they were isolated are: Fny-CMV and Sny-CMV (*Cucumis melo*, New York); O-CMV, Y-CMV, and Le-CMV (*N. tabacum*, Japan); UH-CMV (*Phaseolus vulgaris*, Hungary); T136-CMV (*P. vulgaris*, Turkey); Pg-CMV (*P. vulgaris*, Spain); VE85-CMV (*Malva neglecta*, Iran); SST-CMV (*Lycopersicon esculentum*, New York); MB-CMV (*Vigna radiata*, Sri Lanka); M-CMV and Wh-CMV (*N. tabacum*, UK); F100-CMV (*P. vulgaris*, Italy); PRC-CMV (*L. esculentum*, P.R. China); K-CMV (*Centaurea cyanus*, P.R. China); A9-CMV (*Anemone coronaria*, Italy); LS-CMV (*Lactuca sativa*, New York); U-CMV (*Musa sp.*, Australia); Glad-CMV (*Gladiolus sp.*, Florida); CMV-V26, CMV-V27, and CMV-V28 (*Cucurbita pepo*, California); CMV-NY and CMV-CA (Cornell University); Peanut stunt virus (PSV-76-64) (*P. vulgaris*, Virginia); Tobacco etch virus (TEV) (Oregon); and Tomato aspermy virus strain 1 (TAV), and TMV U1 (Cornell University).

EXAMPLES

EXAMPLE I (cucumber mosaic virus strains)

Cucumber mosaic virus strains (Table 3) were purified from *Nicotiana tabacum* cv. Turkish Samsun as described by Roossinck and Palukaitis [see Mol. Plant-Microbe Interactions 3:188 (1988)]. Viral RNA was isolated from intact cucumber mosaic virus virions by phenol/chloroform extraction and ethanol precipitation. Plants were routinely inoculated with virus in 50 mM sodium phosphate buffer, pH 7.2, or RNA in 50 mM Tris phosphate buffer, pH 8.9, with the use of the abrasive Oelite (plants were also inoculated with sap as inoculum as an alternative method). *Nicotiana tabacura* cv. Turkish Samsun NN was used for plant transformation and as a cucumber mosaic virus-susceptible systemic host. Plants were maintained in a green house or in a growth chamber at 24°-25° C. with a 16 hr/8 hr light-dark cycle.

Alternative mechanical methods of inoculation were also used and reported in Table 3. In this alternative method, the virus was diluted in 0.05M phosphate buffer, pH 7.0, using either Celite or Carborundum as the abrasive. Plants were grown as before in 8 cm diameter pots and inoculated with a glass paddle on two leaves each when the plants were between 3 and 6 cm tall. They were kept for several weeks in a growth chamber held at 24+-25° C. with a 16 hour photoperiod as before to assess resistance. Resistance was routinely determined by visual inspection of symptom expression; in some cases back inoculation to untransformed (NN) tobacco plants or ELISA (plants were assayed for the NPTII protein using an ELISA kit as described by the manufacturer, 5-Prime-3-Prime Inc., and some tobacco plants were also analyzed for the presence of CMV by ELISA using an antiserum prepared against the Fny-strain of CMV [see. Plant Pathology 41:282 (1992)] was used to substantiate the assessment.

EXAMPLE II (modification and subcloning of cucumber mosaic virus RNA-2)

The Fny-CMV cDNA clone pFny206 [see J Gen. Virol. 69:1777 (1988)], which encodes a full length non-infectious RNA-2, was modified and subcloned into a binary plant transformation vector as shown in FIG. 1. This RNA-2 clone was modified by digesting pFny206 with the restriction endonuclease Ncol, phenol/chloroform extracted to remove these enzymes, and ethanol precipitated. This DNA was treated with Klenow fragment in the absence of nucleotides in an attempt to obtain a blunt-ended molecule. This DNA was then digested with the restriction endonuclease BstEII, treated with Klenow fragment in the presence of nucleotides to obtain a blunt ended molecule, phenol/chloroform extracted, and ethanol precipitated. This linear molecule was then recircularized by T4 DNA ligase to generate plasmid (pFnyN/B-4) which contained a cDNA clone of Fny-CMV RNA-2 in which 94 nucleotides from nucleotide 1857 to nucleotide 1950, inclusive, were deleted. This 94 nucleotide region contained the Gly-Asp-Asp domain that is highly conserved among replicase proteins of many positive-sense viruses. This deletion also caused a shift in the open reading frame which resulted in an in-frame translational stop codon 15 codons downstream of the deletion site. This deletion, therefore, not only deleted a 94 bp region, but also resulted in a truncated open reading frame. Cloning also resulted in the retention of an AUG as a potential translation initiator 87 nucleotides upstream of the AUG in the RNA 2 gene resulting in potential translation of an additional 29 amino acids at the amino terminus of the protein. The protein encoded by this modified gene is thus approximately 75 kDa in size compared with a wildtype protein of 96.7 kDa.

To subclone this modified Fny-CMV RNA-2 cDNA clone into a binary plant transformation vector, pN/B-4 was digested with Sph1 which cut this plasmid at a site 5' of the N-terminus of the RNA-2 cDNA deletion clone. An adapter containing a 5' BamH1 overhang and a 3' Sph1 overhang was ligated to this site and then digested with BamH1 which cuts at a site of 3' of the C-terminus, thereby liberating the entire modified cDNA molecule. This 3 kb fragment was subcloned via standard techniques into the BamHI site of the binary plant transformation expression vector pRok2 [see Nature 321:446 (1986)], to generate pCMV N/B-23. This construct was transferred to *Agrobacterium tumefaciens* strain LBA-4404 by tri-parental mating [see Methods Enzymol. 118:627 (1986)] mediated by *E. coli* strain MM294-pRK2013. The transconjugates were selected by kanamycin and streptomycin at 50 and 125 μg/ml respectively. The nucleotide sequence of Fny-CMV RNA-2 in pFny206 and pCMV N/B-23 are shown in FIG. 2.

EXAMPLE III (plant transformation)

Transformation of *Nicotiana tabacum* cv. Turkish Samsun NN was accomplished via *Agrobacterium tumefaciens*-mediated leaf disk transformation described by Horsch [see Science 227:1229 (1985)]. Two days after co-cultivation of the leaf discs with pCMV N/B-23 the leaf discs were transferred to shoot regeneration medium containing 500

μg/ml of carbenicillin, 300 μg/ml of kanamycin, 1 mg/l 6-benzyl aminopurine (BAP), and 0.1 mg/l napthyl acid (NAA). Leaf discs growing in this medium were transferred to fresh medium every 7 to 14 days. By approximately 4 weeks, shoots formed which were transferred to root-inducing medium containing 300 μg/ml of Kanamycin, 0.2 mg/l BAP, and 0.1 mg/l of NAA. These shoots formed roots in approximately 2–3 weeks at which time they were transferred to vermiculite for 2 weeks, repotted to soil, and transferred to a growth chamber. Eighteen independent kanamycin resistant transformants were chosen for further analysis.

EXAMPLE IV (assessment of resistance)

Eighteen independent transformants were initially screened by a detached leaf assay for resistance to Fny-CMV infection. A leaf was removed from each $R_O$ generation transgenic plant and inoculated on the upper and lower epidermis with 50 μg/ml of Fny-CMV. The leaf stems were immersed in water and the leaves were incubated for 6 days at 25° C. after which a leaf disc 2 cm in diameter was removed. Extracts of this tissue were probed with $^{32}$P-labeled cDNA to Fny-CMV to determine if viral RNA was present [see Methods For Plant Biology, Weissbach and Weissbach, eds., Academic Press, New York (1988)]. The absence or presence of viral RNA indicated resistance or susceptibility to virus infection, respectively. These transgenic plants were allowed to flower and seeds of the R1 generation were collected and planted.

This assay indicated that seven of these transgenic lines were resistant to Fny-CMV infection. The R1 generation seedlings from each of the 7 transformed lines which appeared resistant by the detached leaf assay. (N/B 1-1, 1-2, 1-8, 2-3, 2-5, 2-6 and 2-7) as well as one transgenic line (N/B 2-1) which did not show resistance in the detached leaf assay and non-transformed *N. tabacum* cv. Turkish Samsun NN plants were inoculated with 0.2, 1.0, 5, 10 and 100 μg/ml of Fny-CMV. All of the putative resistant lines were either resistant or had a delay in symptoms at inoculum doses between 0.2 and 1.0 μg/ml as depicted in the following Table 1 which provides an assessment of replicase-mediated resistance to CMV infection in R1 generation transgenic tobacco plants:

TABLE 1

| Line[a] | Inoculum Concentration[b] (μg/ml) | | | | | | | |
|---|---|---|---|---|---|---|---|---|
| | 0.2 | 1 | 5 | 10 | 100 | 500 | 20[f] | 50[g] |
| N/B 1-1 | 4/12[c] | 12/12 | 12/12 | 10/10 | 9/10 | ND | ND | ND |
| N/B 1-2 | 1/12 | 13/34 | 2/12 | 17/33 | 16/36 | 21/26 | 8/10 | ND |
| N/B 1-8 | 3/12 | 3/27 | 4/12 | 10/27 | 11/31 | 14/32 | 2/10 | 5/14 |
| N/B 2-3 | ND[e] | 12/23 | ND | 23/25 | 26/26 | 25/25 | ND | ND |
| N/B 2-5 | 6/12 | 10/11 | 12/12 | 10/10 | 10/10 | ND | ND | ND |
| N/B 2-6 | 4/12 | 7/12 | 11/11 | 10/10 | 10/10 | ND | ND | ND |
| N/B 2-7 | 10/12 | 10/12 | 11/11 | 10/10 | 10/10 | ND | ND | ND |
| N/B 2-1 | 12/12 | 31/31 | 11/11 | 28/28 | 26/26 | 27/27 | ND | ND |
| N/N | 3/3 | 4/4 | 4/4 | ND | ND | 3/3 | 4/4 | 4/4 |

[a]A preliminary detached leaf assay had indicated that all of these lines (except line N/B 2-1 and N/N) were resistant to Fny-CMV infection;
[b]Plants were inoculated with Fny-CMV in 50 mM NaPO$_4$ buffer, pH 7.2, with Celite as an abrasive. These data represent the number of plants showing symptoms at two weeks post inoculation as a function of the total number of inoculated plants;
[c]These numbers indicate the number of plants showing systemic symptoms over the total number of plants inoculated;
[e]ND = not determined;
[f]To determine if temperature affected resistance, plants were inoculated with Fny-CMV at 20 μg/ml and incubated at 30° C. for two weeks; and
[g]Plants were inoculated with Fny-CMV RNA at 50 μg/ml in 10 mM Tris-HCl buffer, pH 8.9.

Two lines (N/B 1-2, N/B 1-8) in which the individual plants were resistant to these virus concentrations were tested for resistance to Fny-CMV inoculum concentrations of 500 μg/ml of virus and line inoculated with 50 μg/ml of Fny-CMV RNA. Not all R1 generation plants from these lines were resistant due to Mendelian segregation of this resistance trait within these R1 populations. Plants were scored daily by visual observation of symptom development. In some cases the presence of viral RNA in these inoculated plants was determined by probing leaf extracts with $^{32}$P-labeled Fny-CMV cDNA. R1 seedlings of lines N/B 1-2, 1-8, 2-3, and the two control lines were inoculated with Fny-CMV at 500 μg, and as shown in Table 1, 14 of 32 inoculated N/B 1-8 plants and 21 of 26 inoculated N/B 1-2 plants did develop symptoms of disease. Hence, it appears that very high inoculum doses can overwhelm some plants which might be resistant to lower inoculum doses. This presumption was confirmed in experiments with R2 generation plants where a few plants (3 of 35) which were resistant at 100 μg/ml showed symptoms when superinfected at 500 μg/ml.

Neither viral RNA nor progeny virus could be detected in the uninoculated leaves of resistant plants using dot blot hybridization and bioassay, an indication that these plants exhibited true resistance and not merely symptom suppression.

$R_1$ generation seedlings from two lines (N/B 1-2 and N/B 1-8), a transgenic line (N/B 2-1) which did not show resistance in the detached leaf assay, and non-transformed *Nicotiana tabacum* cv. Turkish Samsun NN plants were also tested for resistance to Fny-CMV infection by viruliferous aphids (*Myzus persicae*). *Nicotiana clevlandii* systemically infected with Fny-CMV acted as the virus source plants on which these aphids fed prior to feeding on the experimental plants. Following a 30 minute feeding period on the source plants these aphids were transferred to the transgenic and control plants with each plant receiving 10 aphids. The aphids were allowed to feed for approximately 15 hr after which the plants were fumigated with insecticide to kill the aphids. The resultant plants were resistant to Fny infection when transmitted by aphids.

In an alternative series of transmission studies, CMV-infected *N. clevelandii* and *Cucurbita pepo* cv Zucchini Elite were used as the sources of virus for acquisition by aphids. In these studies, ten to twenty aphids per target plant were employed, and the plants were held for 17–21 days post-inoculation with any resultant disease symptoms being noted. The results of these studies are depicted and discussed in relation to Table 4.

EXAMPLE V (genomic DNA analysis)

Genomic DNA was isolated from leaf tissue by a modified procedure of Murray and Thompson [see Nuc. Acids Research 8:4321 (1980)]. High molecular weight DNA was digested with restriction enzymes, separated on a 0.8% agarose gel, transferred to GeneScreenPlus (Dupont) nylon membranes. This membrane was hybridized in 5× SSC, 5× Denhardts, 5% dextran sulfate and 2% SDS to a $^{32}$P-labeled DNA probe specific for Fny-CMV RNA-2 gene sequence. All DNA probes were prepared by the random hexamer primer reaction [see Anal. Biochem 132:6 (1983)] to specific activities of at least $5 \times 10^8$ cpm/µg of DNA.

To determine if this resistance was temperature sensitive, R1 seedlings of the resistant lines N/B 1-2 and 1-8, and control lines N/B 2-1 and untransformed *Nicotiana tabacum* cv. Turkish Samsun NN were inoculated with Fny-CMV at 20 µg/ml and immediately placed in a growth chamber maintained at 30° C. Within 4 days after inoculation all of the control plants developed systemic symptoms whereas many N/B 1-2 and 1-8 resistant plants were obtained, indicating that this resistance was not temperature sensitive (see Table 1).

Prior studies [see EMBO J. 6:1845 (1987); Bio/Technology 8:127 (1990), and Virology 159:299 (1987)] have shown that coat protein mediated protection of TMV and alfalfa mosaic virus can sometimes be overcome by inoculation with viral RNA. Therefore, R1 seedlings of line N/B 1-8, the non-resistant N/B 1-2 control line, and non-transformed *Nicotiana tabacum* cv. Turkish Samsun NN line were inoculated with 50 µg/ml of Fny-CMV RNA. While the control lines developed systemic symptoms in 100% of the plants by 4 days, only 36% of the segregating N/B 1-8 plants developed symptoms even after 14 days (Table 1). It is apparent from these data that lines N/B 1-2 and 1-8 are resistant to both virus and viral RNA at very high inoculum levels.

The specificity of resistance was determined by challenging R1 seedlings of the resistant lines N/B 1-2 and the untransformed *Nicotiana tabacum* cv. Turkish Samsun NN with 20 µg/ml of three subgroup I strains (O, Sny, Y, Ve85) and one subgroup II strain (LS). The control lines developed symptoms in 100% of the plants by 7 days after inoculation will all four virus strains tested. Resistant N/B 1-2 and 1-8 plants were obtained when challenged with the three subgroup I strains but not when challenged with the subgroup II strain. This indicates that the resistance obtained as a result of practicing the present invention and obtaining transformed plants with a modified chimeric Fny-CMV RNA-2 gene provides resistance to infection by group I CMV virus strains.

To assess the possible role the copy number may have in determining the level of resistance, both non-resistant and resistant R1 generation N/B 1-2 and 1-8 plants were analyzed. The presence of virus in uninoculated leaves, copy number, and presence of a transcript was determined in these as well as in two control plants. This is illustrated in the following Table 2 which provides a correlation of replicase gene copy number and resistance to CMV in R1 generation plants of segregating lines N/B 1-2 and 1-8 which were inoculated with 100 µg/ml and 500 µg/ml of Fny-CMV virus, respectively.

TABLE 2

| Line | Systemic Symptom[a] | Viral Defective Replicase Presence[b] | Viral Defective Replicase Copy Number[c] | Resistance Gene Transcript[d] |
|---|---|---|---|---|
| 1-2 | − | − | 2 | ND |
|  | + | + | 0 or 1 | ND |
| 1-8 | − | − | 3 to 4 | + |
|  | + | + | 3 to 4 | − |
| N/N[e] | −[f] | − | 0 | − |
|  | +[g] | + | 0 | − |

[a]three symptomatic (susceptible) and three symptomless (resistant) plants were examined in lines N/B 1-2 and 1-8;
[b]the presence of viral RNA in uninoculated leaves was determined by dot blot hybridization [see Palukaitis, Methods for Plant Molecular Biology, Academic Press (New York), pgs 487–506 (1988)] using a Fny-CMV cDNA probe;
[c]the number of defective replicase gene copies per haploid gene was determined by Southern blot hybridization analysis of genomic DNA isolated from each plant using the 35S CaMV promoter as a probe. These genomic DNAs were digested with either HindIII/EcoRI which liberated a 2.75 kb fragment, PstI which liberated a 4.1 kb fragment as well as higher molecular weight fragments due to incomplete digestion of methylated DNA, and HindIII which liberated fragments of various molecular weights depending upon the site of insertion of the modified replicase gene in the genome;
[d]total RNA was isolated from each plant, and 40 µg was run in a formaldehyde 1.2% agarose gel, transferred to Genescreen Plus (DuPont) and hybridized using the NOS terminator sequence as a probe;
[e]the NN control line was *Nicotiana tabacum* cv. Turkish Samsun NN;
[f]uninoculated plant; and
[g]inoculated plant 100 µg/ml Fny-CMV.

Virus, as depicted in Table 2, was shown to be present only in those plants showing systemic symptoms. The copy number in the susceptible N/B 1-2 plants were 0 or 1 per haploid genome, whereas the resistant N/B 1-2 plants each contained 2 copies per haploid genome. This indicated that a copy of the gene is necessary but does not assure resistance, and the presence of multiple copies of the gene does not guarantee that a particular plant will be resistant. This is substantiated by analysis of the N/B 1-8 resistant and susceptible plants which showed that they all have incorporated three to four copies per haploid genome (Table 2).

Many of the resistant plants have chlorotic lesions on the inoculated leaves, however, the level of viral RNA in the inoculated leaves of resistant plants is either very low or not detectable by dot-blot hybridization as compared to non-resistant plants, and in addition, viral RNA has not been detected by dot-blot hybridization in uninoculated leaves of resistant plants. These observations suggest that resistance is due to an inhibition of viral replication at the site of infection. Judging from the spreading symptoms seen on some CMV-inoculated leaves, some virus may move from cell to cell, but it does not invade or survive in the vascular system of the plant, and no systemic virus disease develops.

As noted in Example 1, a mechanical means of inoculation was used to study the resistance to systemic infection by inoculation with CMV strains and other viruses in R2 generation plants of Lines 2 and 5. The results are reported in the following Table 3:

TABLE 3

| Inoculum | | NN | Line 2 | Line 5 |
|---|---|---|---|---|
| subgroup I CMV Strains: | | | | |
| Fny-CMV | (sap)[a] | 2/2[b] | 0/4[c] | 0/4[c] |
|  | (100 µg/ml) | 50/50 | 0/144 | 0/52 |
|  | (500 µg/ml) | 4/4 | 0/10[c] | 0/10[c] |
| Sny-CMV | (100 µg/ml) | 24/24 | 0/39 | 0/9 |
| O-CMV | (100 µg/ml) | 22/22 | 0/39 | 0/9 |
| VE85-CMV | (100 µg/ml) | 6/6 | 0/9 | 0/9 |
| Y-CMV | (sap) | 10/10 | 0/10 | 10/10 |
|  | (sap) | 4/4 | 0/4[c] | 0/4[c] |
| Wh-CMV | (sap) | 6/6 | 0/6 | 0/6 |
| M-CMV | (sap) | 5/5 | 0/5 | 0/.5 |
| F100-CMV | (sap) | 2/2 | 0/4[c] | 0/5[c] |
| UH-CMV | (50 µg/ml RNA) | 6/6 | 0/6 | 0/6 |
| Le-CMV | (50 µg/ml RNA) | 6/6 | 0/6 | 0/6 |
| T136-CMV | (50 µg/ml RNA) | 6/6 | 0/6 | 0/6 |
| PCR-CMV | (sap) | 6/6 | 1/6 | 0/6 |
|  | (sap) | 4/4 | 0/10 | 0/10 |
| subgroup II CMV Strains: | | | | |
| LS-CMV | (100 µg/ml) | 17/20 | 20/20 | 20/20 |
| SST-CMV | (sap) | 6/6 | 6/6 | 6/6 |
| U-CMV | (10 µg/ml) | 15/15 | 14/14 | 13/13 |
| A9-CMV | (sap) | 14/14 | 10/10 | 17/17 |
| CMV Strains not characterized: | | | | |
| CMV-V26 | (squash sap) | 8/8 | 0/8 | 0/8 |
| CMV-V27 | (squash sap) | 8/8 | 0/8 | 0/8 |
| CMV-V28 | (squash sap) | 8/8 | 0/8 | 0/8 |
| CMV-NY | (squash sap) | 8/8 | 0/8 | 0/8 |
| CMV-CA | (squash sap) | 8/8 | 0/8 | 0/8 |
| Glad-CMV | (sap) | 19/20 | 0/14[c] | 0/14[c] |
| Other viruses: | | | | |
| TMV-UI | (100 µg/ml) | 10/10 | 10/10 | 10/10 |
| PSV | (sap) | 16/16 | 11/14 | 16/16 |
| TAV | (sap) | 15/15 | 15/15 | 15/15 |
| TEV | (sap) | 9/9 | 9/9 | 9/9 |

[a] unless specified otherwise, sap is derived from N. tabacum;
[b] number of plants infected/number of plants inoculated;
[c] resistance confirmed by back inoculation of sap prepared from uninoculated leaves and transferred to NN plants;

In most instances, the resistance indicated in Table 3 was assessed by the absence of symptoms, but in some instances the assessment was confirmed by back inoculation to NN tobacco, or by ELISA assays. As seen in Table 3, both lines were resistant to most subgroup I strains and were susceptible to infection by all subgroup II strains tested and to TMV, TEV, PSV, and TAV. With PRC-CMV, one Line 2 plant came down with symptoms, but no symptoms were seen in any Line 5 plants. In addition, resistance was shown to a group of CMV strains which have not been categorized as to subgroup, however, based upon the data in Table 3, it is most likely that these are all subgroup I strains.

In the tests for resistance, two subgroup I strains (MB-CMV and K-CMV) CMV) behaved differently from all the others as depicted in Table 4, below:

TABLE 4

| Inoculum | | NN | Line 2 | Line 5 |
|---|---|---|---|---|
| K-CMV | (tobacco sap) | 3/3[a] | 0/5 | 0/5 |
|  | (1 µg/ml) | 24/24 | 1/24 | 0/23 |
|  | (5 µg/ml) | 25/25 | 11/24 | 1/25 |
|  | (100 µg/ml) | 10/10 | 9/9 | 0/10[b] |
|  | (100 µg/ml) | 25/25 | 21/25 | 1/25 |
|  | (200 µg/ml) | 4/4 | | 1/10[c] |
|  | (1000 µg/ml) | 24/24 | 23/23 | 2/24 |
| MB-CMV | (squash sap) | 10/10 | 10/10 | 10/10 |
|  | (tobacco sap) | 6/6 | 5/5 | 0/6 |
|  | (100 µg/ml) | 6/6 | 5/6 | 0/6 |
|  | (200 µg/ml RNA) | 5/5 | 0/5 | 0/5 |

[a] number of plants infected/number of plants inoculated;
[b] uninoculated leaves of these plants were examined serologically by ELISA with CMV antiserum; eight of 10 gave readings indicating virus infection;
[c] uninoculated leaves of these plants were used as inoculum source to back inoculate NN plants; back inoculated NN plants from both the one Line 5 plant which had shown mild symptoms and two others with no symptoms gave mild symptoms.

These strains are more divergent in sequence from the other subgroup I strains as determined by RNase protection analysis, but were not as divergent as the subgroup II strain LS-CMV. As seen in Table 4, there was a differential response of the two lines to these strains; Line 2 plants were much more susceptible to MB-CMV and K-CMV than were Line 5 plants. Furthermore, breakage of the resistance was inoculum dependent. It can also be seen that plants of Line 5 inoculated with K-CMV usually did not develop symptoms, but did support virus replication. ELISA tests on one group of such plants revealed that 8 out of 10 plants were infected as reported in the Table.

As described above, aphid transmission studies were also performed using CMV-infected N. clevelandii and Curcurbita pepo cv Zucchini Elite. In these studies, aphids were used to transmit several CMV strains to determine if the resistance observed upon mechanical inoculation would be retained when the inoculation was made by insects. The following Table 5 provides the data collected:

TABLE 5

| | | | Number Infected Plants/Total[a] | | | | |
|---|---|---|---|---|---|---|---|
| | | | $R_1$ generation | | | $R_2$ generation | |
| Virus Strain | Group | Samsun NN | Line-1[d] | Line-2 | Line-5 | Line-2 | Line-5 |
| Fny-CMV | I | 8/8[b] | 20/20[b] | 6/20[b] | 3/20[b] | | |
|  |  | 5/5[b] |  |  |  | 0/5[b] | 0/4[b] |
| VE85-CMV | I | 4/5[c] |  |  |  | 0/5[c] | 0/5[c] |
| LS-CMV | II | 7/10[c] |  |  |  | 5/10[c] | 4/10[c] |
|  |  | 3/5[b] |  |  |  | 3/5[b] | 1/5[b] |

[a] plants rated by symptom expression and held for 17 to 21 days post inoculation;
[b] transmissions performed with 10 aphids per target plant;
[c] transmissions performed with 20 aphids per target plant
[d] this line was transformed, but exhibited no resistance to mechanical inoculation with Fny-CMV; in Proc. Natl. Acad. Sci USA 89:8759 (1992), this is referred to as Line 2-1.

As indicated in Table 5, the two subgroup I strains, Fny-CMV and VE85-CMV, resistance was observed in both the $R_1$ and $R_2$ generation plants. The $R_1$ generation plants were from an unselected population which was segregating for resistance, hence, some plants became infected. This is in contrast to the $R_2$ generation in which all of the plants were resistant. Resistance was not observed with the Subgroup II strain LS-CMV, consistent with results obtained utilizing mechanical techniques of inoculation as reported in Table 3.

EXAMPLE VI (Southern analysis of plant DNA)

This procedure is a modification of that reported previously in Example V.

Tobacco DNA was prepared by the methods of either Doyle et al [see Focus (Bethesda Research Laboratories) 12:13 (1990)] or Murray et al [see Nucleic Acids Research 8:4321 (1984)]. Restriction digestion, Southern hybridization, and DNA manipulations were performed according to Maniatis [see Molecular Cloning: A Laboratory manual, 2nd ed. Cold Spring Harbor Laboratory (1989)]. A 1 kb DNA ladder (Bethesda Research Laboratories) was used as a molecular weight standard. A 2.9 kb SaII fragment from pFny209 [see Molecular and General Genetics 222:249 (1990)] was radiolabeled by an oligolabeling procedure [see Analytical Biochemistry 132:6 (1983)]. The probe was used at approximately $1.5 \times 10^8$ cpm/ml.

To quantify the number of copies of the modified replicase gene in the transgenic lines, plant DNAs were probed with a radiolabeled cDNA probe, derived from Fny-CMV RNA 2. DNAs prepared from three generations of each of the transgenic lines (Lines 2 and 5) were digested with the restriction enzyme EcoR1 and probed in a Southern hybridization. The probe hybridized with multiple DNA fragments in the transgenic lines, including a 5.5 kbp fragment that was also detected in the untransformed control. Digestion of the transgene with EcoR1 was expected to yield an internal 1.3 kb fragment; this was observed in all of the transgenic lines. EcoR1 cleavage also released fragments that contain sequences from both the transgene and the plant genome; these are unique to each insertion site and their size is dependent upon the location of the EcoR1 site in the plant genome that which is proximal to the 3'-end of the transgene. Hybridization with DNAs from Line 2 revealed three primary bands in all three generations suggesting that there are three copies or three distinct insertion sites. With Line 5, seven EcoR1 fragments hybridized with the probe indicating a larger number of copies of the transgene are present. At least two of these fragments were absent in the third generation suggesting that these transgene copies were segregating and were not required for the resistance phenotype.

The Southern hybridization analyses demonstrated that the transgenic Lines 2 and 5 are independent transformants and that in both lines the transgene has been transferred to multiple sites in the tobacco genome. It is difficult to ascertain with certainty precisely how many insertions have occurred, however, results obtained in Southern hybridizations with DNAs digested by a different enzyme, HindIII, also support the conclusion that in Line 2 there are three different transgene insertion sites, and that in Line 5 there are a larger number of insertions. The maintenance of all three EcoR1 fragments in subsequent generations of Line 2 indicates that these genes are consistently found with the resistance phenotype.

The present invention demonstrates that many subgroup I CMV strains closely related to Fny-CMV are unable to cause systemic disease in the two lines of plants tested. However, the two lines of plants behaved very differently in their response to subgroup I strains MB-CMV and K-CMV in which some resistance breaking was observed as depicted in Table 4. Plants of Line 2 were more susceptible than those of Line 5, an observation that is consistent with the findings of others who found that in in vitro-infected protoplasts derived from these lines, replication was suppressed 60- to 70-fold in Line 5, but was suppressed only 10-fold in protoplasts derived from Line 2.

Plants of these two lines were not resistant to the four subgroup II strains tested, demonstrating that the replicase-mediated resistance according to the present invention's findings are not mimicking classical cross protection [see Annual Review of Phytopathology 24:67 (1986)], as subgroup II strain LS-CMV was found to be able to protect plants against the symptoms of the subgroup I strain Y-CMV.

In conclusion, the data reported herein clearly show that transgenic plants containing a modified CMV-replicase gene are highly resistant to CMV disease. Furthermore, the level of CMV replicase mediated resistance is maintained at an inoculum dose of 500 μg/ml which is 10-fold higher than that previously shown for CMV coat protein mediated protection [see Bio/Technology 6:549 (1988)]. In the preferred embodiment using CMV described herein, replicase sequences, specifically those that do not involve a read-through replicase gene, were used for the plant transformation. It appears that this replicase-mediated resistance is generic and applicable to other plant and animal RNA viruses such as Potato Virus X (PVX is a +strand ss RNA virus and type member of the potexvirus group) and Potato Virus Y. As mentioned above, the replicase sequence motifs and other sequences characteristic of viral replicases are common to a wide range of viral types, not only those infecting plants, but also many with animal hosts [see J. Gen. Virol. 72:217 (1991)]. Based upon an analogy of what has been disclosed herein, it may also be possible to suppress replication of animal viruses in animals by the prior insertion of non-readthrough portions of replicase sequence motifs into the host animal's genome.

Thus, while we have illustrated and described the preferred embodiment of our invention, it is to be understood that this invention is capable of variation and modification, and we therefore do not wish or intend to be limited to the precise terms set forth, but desire and intend to avail ourselves of such changes and modifications which may be made for adapting the present invention to various usages and conditions. Accordingly, such changes and modifications are properly intended to be within the full range of equivalents, and therefore within the purview of the following claims. The terms and expressions which have been employed in the foregoing specification are used therein as terms of description and not of limitation, and thus there is no intention, in the use of such terms and expressions, of excluding equivalents of the features shown and described, or portions thereof, it being recognized that the scope of the invention is defined and limited only by the claims which follow.

Among such modifications are, for example, the substitution of plant transformation vectors other than those specified in the examples above. For example, vectors which are within the range of substitutes or equivalents are those such as pBIN19, pBI101, pRok1, pAGS135, pARC12, PGA470, pRAL3940, and pCT1T3, among others. Although the present invention has been exemplified with CMV, other plant viruses such as, alfalfa mosaic, members of the potexvirus, bromovirus, potyvirus and luteovirus groups which also contain viral replicase regions within their genomes are also encompassed by the present invention, as are the host plants transformed with genetic sequences related to the replicase portions of these viruses. Since it is known that similarities in sequences exist between the replicase regions of RNAs of many "unrelated" plant viruses [see for example, Nucleic Acids Research 19:217 (1989)], including similarities between certain plant and animal RNA viruses, these are properly considered to be equivalents and therefore encompassed by the scope of the present invention.

The listing of all nucleic acid and amino acid sequences contained in this disclosure are reproduced in the following Sequence Listing:

---

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 132 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:1:

```
AAU  ACC  AUC  GUC  ACC  AUG  GCU  GAG  UUU  GCC  UGG  UGU  UAU  GAC    42
ACC  GAC  CAA  UUC  GAA  AAG  CUU  UUA  UUC  UCA  GGC  GAU  GAU  UCU    84
CUA  GGA  UUU  UCA  CUG  CUU  CCC  CCU  GUU  GGU  GAC  CCG  AGU  AAA   126
UUC  ACA      132
```

( 2 ) INFORMATION FOR SEQ ID NO:2:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Asn  Thr  Ile  Val  Thr  Met  Ala  Glu  Phe  Ala  Trp  Cys  Tyr  Asp  Thr
                     5                        10                         15

Asp  Gln  Phe  Glu  Lys  Leu  Leu  Phe  Ser  Gly  Asp  Asp  Ser  Leu  Gly
                    20                        25                         30

Phe  Ser  Leu  Leu  Pro  Pro  Val  Gly  Asp  Pro  Ser  Lys  Phe  Thr
                    35                        40
```

( 2 ) INFORMATION FOR SEQ ID NO:3:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:3:

```
ACC  AUC  GUC  ACC  AUG  GUG  ACC  CGA  GUA  AAU  UCA  CAA  CUC  UUU   42
UCA  ACA  UGG  AAG  CUA  AGG  UGA      63
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Thr Ile Val Thr Met Val Thr Arg Val Asn Ser Gln Leu Phe Ser
    5                   10                      15
Thr Trp Lys Leu Arg
    20

Having thus described our invention and the manner and process of making and using it in such full, clear, concise, and exact terms so as to enable any person skilled in the art to which it pertains, or to with which it is most nearly connected, to make and use the same,

We claim:

1. A DNA molecule comprising:

a promoter region;

a structural gene encoding a replicase protein or polypeptide for a plant pathogenic virus which does not have a replicase read through portion, wherein said structural gene is operably linked to said promoter region; and a 3' non-translated region which is operably linked to said structural gene and functions in plant cells to cause the termination of transcription.

2. An isolated DNA molecule according to claim 1, wherein the plant pathogenic virus is selected from the group consisting of cucumovirus, alfamovirus, bromovirus, luteovirus, potexvirus, and potyvirus.

3. An isolated DNA molecule according to claim 2, wherein the plant pathogenic virus is cucumber mosaic virus.

4. An isolated DNA molecule according to claim 3, wherein the protein or polypeptide has an amino acid sequence corresponding to SEQ. ID. NO. 4.

5. An isolated DNA molecule according to claim 4, wherein the protein or polypeptide is the same as that formed by translation of the nucleic acid sequence corresponding to SEQ. ID. NO. 3.

6. An expression vector containing a DNA molecule encoding a replicase protein or polypeptide for a plant pathogenic virus which does not have a replicase read through portion.

7. An expression vector according to claim 6, wherein the plant pathogenic virus is selected from the group consisting of cucumovirus, alfamovirus, bromovirus, luteovirus, potexvirus, and potyvirus.

8. An expression vector according to claim 6, wherein the DNA molecule is present in the expression vector in proper sense orientation and correct reading frame.

9. A transgenic plant cell transformed to express a DNA molecule encoding a replicase protein or polypeptide for a plant pathogenic virus which does not have a replicase read through portion.

10. A plant cell according to claim 9, wherein the plant pathogenic virus is selected from the group consisting of cucumovirus, alfamovirus, bromovirus, luteovirus, potexvirus, and potyvirus.

11. A plant cell according to claim 9, wherein the DNA molecule is in an expression vector.

12. A transgenic plant seed transformed to express a DNA molecule encoding a replicase protein or polypeptide for a plant pathogenic virus which does not have a replicase read through portion.

13. A plant seed according to claim 12, wherein the plant pathogenic virus is selected from the group consisting of cucumovirus, alfamovirus, bromovirus, luteovirus, potexvirus, and potyvirus.

14. A transgenic plant transformed to express a DNA molecule encoding a replicase protein or polypeptide for a plant pathogenic virus which does not have a replicase read through portion.

15. A plant according to claim 14, wherein the plant pathogenic virus is selected from the group consisting of cucumovirus, alfamovirus, bromovirus, luteovirus, potexvirus, and potyvirus.

16. A plant according to claim 15, wherein the plant pathogenic virus is cucumber mosaic virus.

17. A plant according to claim 16, wherein the protein or polypeptide has an amino acid sequence corresponding to SEQ. ID. NO. 4.

18. A plant according to claim 17, wherein the protein or polypeptide is the same as that formed by translation of the nucleic acid sequence corresponding to SEQ. ID. NO. 3.

19. A method of imparting disease resistance to plants comprising:

forming a transgenic plant cell transformed to express a DNA molecule encoding a replicase protein or polypeptide for a plant pathogenic virus which does not have a replicase read through portion.

20. A method according to claim 19, wherein the plant pathogenic virus is selected from the group consisting of cucumovirus, alfamovirus, bromovirus, luteovirus, potexvirus, and potyvirus.

21. A method according to claim 19, further comprising: propagating a plant from said plant cell after said transforming.

22. A method according to claim 19, wherein said transforming comprises:

infecting the plant cell with *Agrobacterium tumefaciens* containing the DNA molecule.

* * * * *

UNITED STATES PATENT AND TRADEMARK OFFICE
CERTIFICATE OF CORRECTION

PATENT NO. : 5,633,449

DATED : May 27, 1997

INVENTOR(S) : Zaitlin et al.

It is certified that error appears in the above-identified patent and that said Letters Patent is hereby corrected as shown below:

ON THE TITLE PAGE:

Under heading [56] References Cited, on page 1, in the citation identified as Young et al., "Barley Yellow Dwarf Virus Expression in Wheat Protoplasis and Construction of Synthetic Genes to Interfere with Viral Replication," replace "Protoplasis" with --Protoplasts--.

Column 1, line 15, replace "nunnber" with --number--; line 34, replace "or" with --of--.

Column 2, line 45, replace "refers" with --refer--.

Column 4, lines 8, the underlined portions should read as follows:
should read as follows:

CC AUG G

Signed and Sealed this

Twenty-eighth Day of December, 1999

Attest:

Q. TODD DICKINSON

Attesting Officer    Acting Commissioner of Patents and Trademarks

UNITED STATES PATENT AND TRADEMARK OFFICE
CERTIFICATE OF CORRECTION

PATENT NO. : 5,633,449                      Page 2 of 2
DATED      : May 27, 1997
INVENTOR(S) : Zaitlin et al.

It is certified that error appears in the above-identified patent and that said Letters Patent is hereby corrected as shown below:

Column 4, lines 40-47, the underlined portion should read as follows:

<u>CC AUG GUG ACC</u>

Column 5, line 46, replace "Oelite" with --Celite--; line 48, replace "*tabacura*" with --*tabacum*--; line 60, replace "24+-25" with --24-25--.

Column 6, line 2, insert --;-- after CMV and delete the period after "see"; line 46, delete "of".

Column 7, line 60, delete the period after "assay"; line 64, delete "and" and insert a comma between "10" and "100" and insert --and 500-- after "100".

Column 8, line 58, replace "*clevlandii*" with --*clevelandii*--; line 66, replace "Fny" with --Fny-CMV--.

Column 9, line 55, replace "will" with --with--.

Column 12, line 6, delete "CMV)" before "behaved".

Column 13, line 1, insert --with-- before "the";